(12) United States Patent
Surtees et al.

(10) Patent No.: US 7,629,474 B2
(45) Date of Patent: Dec. 8, 2009

(54) PROCESS FOR PREPARING 2-OXO-1-PYRROLIDINE DERIVATIVES

(75) Inventors: John Surtees, Jezus-Eik-Overijse (BE); Françoise Lurquin, Villers-la-Ville (BE); Ousmane Diouf, Les Côtes d'Arey (FR)

(73) Assignee: UCB Pharma S.A., Brussels (BE)

( * ) Notice: Subject to any disclaimer, the term of this patent is extended or adjusted under 35 U.S.C. 154(b) by 511 days.

(21) Appl. No.: 10/572,579

(22) PCT Filed: Sep. 13, 2004

(86) PCT No.: PCT/EP2004/010212

§ 371 (c)(1), (2), (4) Date: Jan. 3, 2007

(87) PCT Pub. No.: WO2005/028435

PCT Pub. Date: Mar. 31, 2005

(65) Prior Publication Data

US 2007/0100150 A1    May 3, 2007

(30) Foreign Application Priority Data

Sep. 24, 2003 (EP) .................................. 03021534

(51) Int. Cl.
*C07D 207/26* (2006.01)

(52) U.S. Cl. ..................................................... 548/554
(58) Field of Classification Search .................. None
See application file for complete search history.

(56) References Cited

FOREIGN PATENT DOCUMENTS

| EP | 0 162 036 | 11/1985 |
|----|-----------|---------|
| GB | 2 225 322 | 5/1990 |
| WO | 01/62726 | 8/2001 |
| WO | 02/076451 | 10/2002 |
| WO | 02/094787 | 11/2002 |
| WO | 03/014080 | 2/2003 |

*Primary Examiner*—Kamal A Saeed
(74) *Attorney, Agent, or Firm*—Oblon, Spivak, McClelland, Maier & Neustadt, L.L.P.

(57) ABSTRACT

The present invention relates to a new process for preparing 2-oxo-I-pyrrolidine derivatives of general formula (I) wherein the substituents are as defined in the specification.

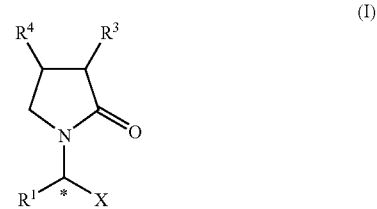

18 Claims, No Drawings

PROCESS FOR PREPARING 2-OXO-1-PYRROLIDINE DERIVATIVES

The invention concerns a process for preparing 2-oxo-1-pyrrolidine derivatives.

(S)-(−)-α-ethyl-2-oxo-1-pyrrolidine acetamide, which is referred under the International Nonproprietary Name of Levetiracetam,

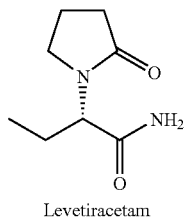

Levetiracetam is disclosed as a protective agent for the treatment and the prevention of hypoxic and ischemic type aggressions of the central nervous system in the European patent No. 0 162 036. This compound is also effective in the treatment of epilepsy.

The preparation of Levetiracetam has been described in the European patent No. 0 162 036 and in the British patent No. 2 225 322.

Other derivatives of 2-oxo-1-pyrrolidine and their synthesis have been disclosed in WO 01/62726. This patent application specifically discloses the synthesis of (2S)-2-(2-oxo-4-n-propyl-1-pyrrolidinyl)butanamide using a two-step reaction wherein, in the first step, 4-n-propyl-hydroxyfuranone is reacted with S-2-aminobutyramide in the presence of $NaBH_4$ in order to form and isolate the corresponding unsaturated pyrrolidone, followed by a second reaction step, wherein the unsaturated pyrrolidone is hydrogenated with $NH_4COOH$ in the presence of a Pd/C catalyst.

The present invention relates to a simple and more economical process for the preparation of 2-oxo-1-pyrrolidine derivatives.

The invention provides a process for the preparation of 2-oxo-1-pyrrolidine derivatives of general formula (I), and salts thereof,

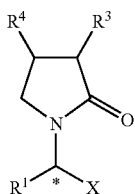

wherein:
$R^1$ is $R^a$ or $R^b$;
$R^3$ and $R^4$ are the same or different and each is, independently, hydrogen, hydroxy, thiol, halogen, cyano, carboxy, sulfonic acid, $R^a$, $R^b$, alkylsulfonyl, arylsulfonyl, alkylsulfinyl, arylsulfinyl, alkylthio, arylthio, alkoxy, aryloxy, sulfonamide, acyl, ester, amido, acyloxy, esteroxy or amidooxy;
X is $-CONR^5R^6$, $-COOR^7$ or $-CN$;
$R^5$, $R^6$, $R^7$ are the same or different, and each is, independently, hydrogen, $R^a$ or $R^b$;
$R^a$ is C1-20 alkyl or C1-20 alkyl substituted by one or more hydroxy, thiol, halogen, cyano, carboxy, sulfonic acid, $R^b$, alkylsulfonyl, arylsulfonyl, alkylsulfinyl, arylsulfinyl, alkylthio, arylthio, alkoxy, aryloxy, sulfonamide, acyl, ester, amido, acyloxy, esteroxy and/or amidooxy;
$R^b$ is aryl, heteroaryl, heterocycloalkyl or the same substituted by one or more $R^a$, hydroxy, thiol, halogen, cyano, carboxy, sulfonic acid, aryl, alkylsulfonyl, arylsulfonyl, alkylsulfinyl, arylsulfinyl, alkylthio, arylthio, alkoxy, aryloxy, sulfonamide, heterocycloalkyl, heteroaryl, acyl, ester, amido, acyloxy, esteroxy and/or amidooxy;

comprising the reaction of a furan derivative of formula (II) or (III)

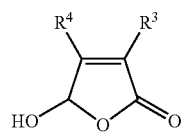

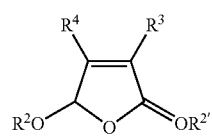

wherein $R^2$ and $R^{2'}$ are the same or different and each is C1-10 alkyl or the same substituted by aryl,
with a compound of formula (IV)

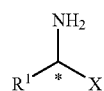

and with $H_2$ in the presence of catalyst.

The term "alkyl", as used herein, is defined as including saturated monovalent hydrocarbon radicals having straight, branched or cyclic moieties or combinations thereof and containing 1-20 carbon atoms, preferably 1-6 carbon atoms for non-cyclic alkyl and 3-8 carbon atoms for cycloalkyl.

The term "aryl" as used herein, includes an organic radical derived from an aromatic hydrocarbon by removal of one hydrogen, such as phenyl, naphthyl.

The term "heterocycloalkyl", as used herein, represents a cyclic alkyl (cycloalkyl), having at least one O, S and/or N atom interrupting the carbocyclic ring structure such as tetrahydrofuranyl, tetrahydropyranyl, piperidinyl, piperazinyl, morpholino and pyrrolidinyl groups.

The term "heteroaryl", as used herein, represents an "aryl" as defined above, having at least one O, S and/or N interrupting the carbocyclic ring structure, such as pyridyl, furyl, pyrrolyl, thienyl, isothiazolyl, imidazolyl, benzimidazolyl, tetrazolyl, pyrazinyl, pyrimidyl, quinolyl, isoquinolyl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

The term "halogen", as used herein, includes an atom of Cl, Br, F, I.

The term "hydroxy", as used herein, represents a group of formula —OH.

The term "thiol", as used herein, represents a group of formula —SH.

The term "cyano", as used herein, represents a group of formula —CN.

The term "carboxy", as used herein, represents a group of formula —COOH.

The term "sulfonic acid", as used herein, represents a group of formula —$SO_3H$.

The term "sulfonamide", as used herein, represents a group of formula —$SO_2NH_2$ in which one or both of the hydrogen may optionally be replaced by "alkyl", "aryl", "heteroaryl" and/or "heterocycloalkyl" or the same substituted as defined above.

The term "acyl" as used herein, represents a group of formula RCO—, wherein R represents an "alkyl", "aryl", a "heterocycloalkyl" or "heteroaryl" moiety, or the same substituted as defined above.

The term "ester", as used herein, represents a group of formula —COOR wherein R represents an "alkyl", "aryl", a "heterocycloalkyl" or "heteroaryl" moiety, or the same substituted as defined above.

The term "alkoxy", as used herein, includes —OR groups wherein R represents an "alkyl" or a "heterocycloalkyl" moiety, or the same substituted as defined above.

The term "aryloxy", as used herein, includes —OR groups wherein R represents an "aryl" or a "heteroaryl" moiety, or the same substituted as defined above.

The term "alkylthio" as used herein, includes —SR groups wherein R represents an "alkyl" or a "heterocycloalkyl" moiety, or the same substituted as defined above.

The term "arylthio", as used herein, includes —SR groups wherein R represents an "aryl" or a "heteroaryl" moiety, or the same substituted as defined above.

The term "acyloxy", as used herein, represents a group of formula RCOO—, wherein R represents an "alkyl", "aryl", a "heteroaryl" or "heterocycloalkyl" moiety, or the same substituted as defined above.

The term "alkylsulfonyl", as used herein, represents a group of formula —$SO_2R$ wherein R represents an "alkyl" or a "heterocycloalkyl" moiety, or the same substituted as defined above.

The term "arylsulfonyl", as used herein, represents a group of formula —$SO_2R$ wherein R represents an "aryl" or a "heteroaryl" moiety, or the same substituted as defined above.

The term "alkylsulfinyl", as used herein, represents a group of formula —SO—R wherein R represents an "alkyl" or a "heterocycloalkyl" moiety, or the same substituted as defined above.

The term "arylsulfinyl", as used herein, represents a group of formula —SO—R wherein R represents an "aryl" or a "heteroaryl" moiety, or the same substituted as defined above.

The term "esteroxy", as used herein, represents a group of formula —OCOOR, wherein R represents an "alkyl", "aryl", a "heteroaryl" or "heterocycloalkyl" moiety, or the same substituted as defined above.

The term "amido", as used herein, represents a group of formula —$CONH_2$ in which one or both of the hydrogen atoms may optionally be replaced by "alkyl", "aryl", "heteroaryl" and/or "heterocycloalkyl" or the same substituted as defined above.

The term "amidooxy", as used herein, represents a group of formula —$OCONH_2$ in which one or both of the hydrogen atoms may optionally be replaced by "alkyl", "aryl", "heteroaryl" and/or "heterocycloalkyl" or the same substituted as defined above.

In the process according to the present invention, $R^a$ is preferably C1-20 alkyl or C1-20 alkyl substituted by one or more hydroxy, thiol, halogen, cyano, carboxy, sulfonic acid, aryl, alkylsulfonyl, arylsulfonyl, alkylsulfinyl, arylsulfinyl, alkylthio, arylthio, alkoxy, aryloxy, sulfonamide, heterocycloalkyl, heteroaryl, acyl, ester, amido, acyloxy, esteroxy and/or amidooxy; and $R^b$ is preferably aryl, heteroaryl, heterocycloalkyl or the same substituted by one or more alkyl, hydroxy, thiol, halogen, cyano, carboxy, sulfonic acid, aryl, alkylsulfonyl, arylsulfonyl, alkylsulfinyl, arylsulfinyl, alkylthio, arylthio, alkoxy, aryloxy, sulfonamide, heterocycloalkyl, heteroaryl, acyl, ester, amido, acyloxy, esteroxy and/or amidooxy.

In the compounds of formula (I) and (V),

X is preferably —$CONR^5R^6$, more preferably —$CONH_2$.

$R^1$ is preferably C1-6 alkyl, more preferably methyl, ethyl, n-propyl, isopropyl, n-butyl, or isobutyl; most preferably methyl, ethyl or n-propyl, especially ethyl.

A furan derivative of formula (II) is preferably used in the process of the present invention.

In the compounds of formula (I), (II) and (III), $R^3$ is preferably hydrogen, halogen or a C1-4 alkyl. More preferably $R^3$ is hydrogen.

When a furan derivative of formula (II) is used, $R^4$ is preferably $R^a$ or hydrogen, more preferably C1-6 alkyl or C1-6 alkyl substituted by one or more halogens. Most preferably, $R^4$ is n-propyl.

When a furan derivative of formula (III) is used, $R^3$ and $R^4$ are preferably the same. In that case, $R^3$ and $R^4$ are more preferably selected from hydrogen, halogen or a C1-4 alkyl. Most preferably, $R^3$ and $R^4$ are hydrogen.

In the furan derivatives of formula (III), $R^2$ and $R^{2'}$ are preferably C1-4 alkyl or benzyl, most preferably methyl.

The compounds of formulae (I) and (II) used in the process according to the invention can be obtained by any process suitable therefore.

Compounds of formula (II) are preferably obtained by reaction of an aldehyde of formula (V) with a ketoacid of formula (VI) in the presence of a base such as a cyclic secondary amine, preferably morpholine, followed by hydrolysis in acidic conditions. The reaction is generally conducted at a temperature comprised between 25° C. and 100° C., preferably between 30° C. and 60° C. More preferably, the reaction product is purified by extraction, particularly with an ether, especially diisopropyl ether.

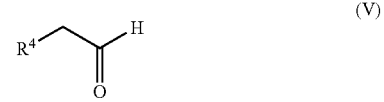

(V)

(VI)

The present invention therefore also relates to the preparation of compounds of formula (II) by the process mentioned here above.

The compound of formula (IV) used in the process according to the invention can be obtained by any means suitable therefore. It is preferably obtained by neutralisation of the corresponding salts, more preferably from the corresponding hydrochloride or tartaric acid salt, most preferably from the corresponding hydrochloride salt.

The process according to the invention is generally conducted in the presence of solvent.

Preferred solvents are selected from alcohols, water, esters such as ethyl acetate and aromatic solvents such as toluene or mixtures thereof. More preferred solvents are alcohols. Most preferred is isopropanol.

Preferred catalysts according to the invention are metal based catalysts, such as Pd, Pt and Ni based catalysts. More preferred are Pd based catalysts, most preferably Pd on C such as 5% Pd on carbon.

The reaction is generally carried out at a temperature of from 25° C. to 100° C., preferably 30° C. to 60° C., most preferably 40° C.

The process according to the invention is conducted in the presence of hydrogen. The process according to the invention is generally conducted under hydrogen pressure in the range of 0.1 to 10 bar, preferably 0.2 to 5 bar and most preferably 0.2 to 0.5 bar, in a closed reactor.

The process according to the present invention is also applicable to the preparation of pharmaceutically acceptable salts of compound (I).

The term "pharmaceutically acceptable salts" according to the invention includes therapeutically active, non-toxic base and acid addition salt forms which the compounds of formula (I) are able to form.

The process according to the invention relates to the preparation of all stereoisomeric forms such as geometrical and optical enantiomeric and diastereoisomeric forms of the compounds of formula (I) and mixtures (including racemates) thereof. The compounds of formula (I) and (IV) have at least one stereogenic center in their structure, being the carbon atom attached to the nitrogen atom of the pyrrolidine ring. This stereogenic center is indicated by an asterisk (*) in compounds of formula (I) and (IV). This stereogenic center may be present in a R or S configuration, said R and S notation is used in accordance with the rules described in Pure. Appl. Chem., 45 (1976) 11-30.

The process according to the invention preferably applies to the preparation of compounds of formula (I) in the (S)- or in the (R)-form.

The term "(S)-form", as used herein, means that the compound in question is composed of more than 50%, preferably more than 90% of the enantiomer having the stereogenic carbon atom indicated by an asterisk in the S configuration.

The term "(R)-form", as used herein, means that the compound in question is composed of more than 50%, preferably more than 90% of the enantiomer having the stereogenic carbon atom indicated by an asterisk in the R configuration.

The process according to the invention is particularly suited for the preparation of compounds of general formula (I) in the (S)-form.

In this case, the process according to the invention is preferably conducted by using a compound of formula (IV) in the (S)-form or in the (R)-form.

It was surprisingly found that no racemization occurs during the process of the present invention.

When $R^3$ and/or $R^4$ are different from hydrogen, the compounds of formula (I) have at least one supplementary stereogenic center in their structure, that is the carbon atom to which such $R^3$ and $R^4$ is attached.

In that case, the process may contain a further step wherein the obtained diastereoisomers are separated. Such separation can be done by any means suitable therefore. It is preferably done by chromatography, in particular using a chiral stationary phase.

The process according to the invention particularly applies to the preparation of compounds of formula (I) in the (2S,4S) and (2S,4R) form. The term (2S,4S) [respectively (2S,4R)] as used herein means that the compound in question is composed of more than 50%, preferably more than 90% of the diastereoisomer having the stereogenic carbon atom indicated by an asterisk in the S configuration and the carbon atom to which $R^4$ is attached in the S configuration [respectively R configuration].

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLE 1

Synthesis of (2S)-2-((4R)-2-oxo-4-n-propyl-1-pyrrolidinyl)butanamide 1.1 Synthesis of (2S)-2-aminobutyramide Free Base

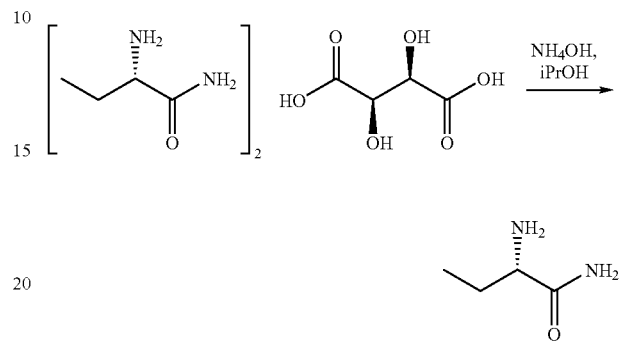

1800 ml of isopropanol are introduced in a 5 L reactor. 1800 g of (2S)-2-aminobutyramide tartrate are added under stirring at room temperature. 700 ml of a 25% aqueous solution of ammonium hydroxide are slowly added while maintaining the temperature below 25° C. The mixture is stirred for an additional 3 hours and then the reaction is allowed to complete at 18° C. for 1 hour. The ammonium tartrate is filtered. Yield: 86%.

1.2 Synthesis of 5-hydroxy-4-n-propyl-furan-2-one

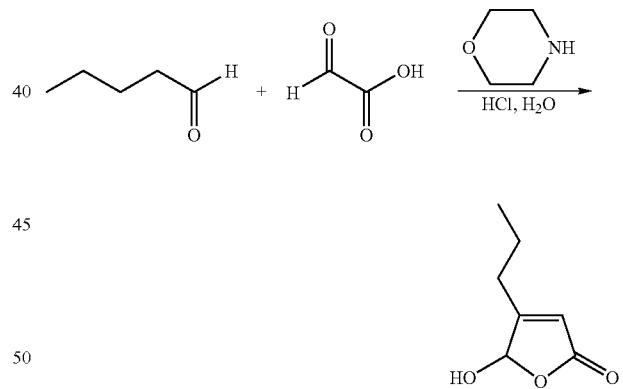

Heptane (394 ml) and morpholine (127.5 ml) are introduced in a reactor. The mixture is cooled to 0° C. and glyoxylic acid (195 g, 150 ml, 50 w % in water) is added. The mixture is heated at 20° C. during 1 hour, and then valeraldehyde (148.8 ml) is added. The reaction mixture is heated at 43° C. during 20 hours. After cooling down to 20° C., a 37% aqueous solution of HCl (196.9 ml) is slowly added to the mixture, which is then stirred during 2 hours.

After removal of the heptane phase, the aqueous phase is washed three times with heptane. Diisopropyl ether is added to the aqueous phase. The organic phase is removed, and the aqueous phase further extracted with diisopropyl ether (2×). The diisopropyl ether phases are combined, washed with brine and then dried by azeotropic distillation. After filtration and evaporation of the solvent, 170 g of 5-hydroxy-4-n-propyl-furan-2-one are obtained as a brown oil. Yield: 90.8%

1.3 Synthesis of (2S)-2-((4R)-2-oxo-4-n-propyl-1-pyrrolidinyl)butanamide and (2S)-2-((4S)-2-oxo-4-n-propyl-1-pyrrolidinyl)butanamide

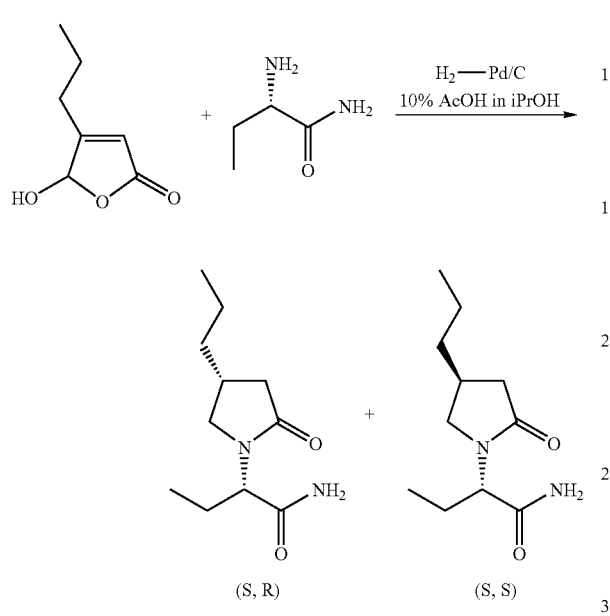

The (2S)-2-aminobutyramide solution in isopropanol containing 250 g obtained as described here above is dried by azeotropic distillation under vacuum. To the dried (2S)-2-aminobutyramide solution is added 5-hydroxy-4-n-propyl-furan-2-one (290 g) between 15° C. and 25° C.; the mixture is heated to 30° C. and kept for at least 2 hours at that temperature. Acetic acid (1.18 eq.), Pd/C catalyst (5 w/w %; Johnson Matthey 5% Pd on carbon—type 87L) are then added and hydrogen introduced into the system under pressure. The temperature is kept at 40° C. maximum and the $H_2$ pressure maintained between 0.2 bar and 0.5 bar followed by stirring for at least 20 hours following the initial reaction. The solution is then cooled to between 15° C. and 25° C. and filtered to remove the catalyst. The solution of product in isopropanol is solvent switched to a solution of product in isopropyl acetate by azeotropic distillation with isopropyl acetate. The organic solution is washed with aqueous sodium bicarbonate followed by a brine wash and then filtered. After recrystallisation, 349 g of (2S)-2-((4R)-2-oxo-4-n-propyl-1-pyrrolidinyl)butanamide and (2S)-2-((4S)-2-oxo-4-n-propyl-1-pyrrolidinyl)butanamide are obtained (Yield: 82.5%).

1.4 Preparation of (2S)-2-((4R)-2-oxo-4-n-propyl-1-pyrrolidinyl)butanamide

The chromatographic separation of the two diastereoisomers obtained in 1.3 is performed using of (CHIRALPAK AD 20 μm) chiral stationary phase and a 45/55 (volume/volume) mixture of n-heptane and ethanol as eluent at a temperature of 25±2° C.

The crude (2S)-2-((4R)-2-oxo-4-n-propyl-1-pyrrolidinyl) butanamide thus obtained is recrystallised in isopropylacetate, yielding pure (2S)-2-((4R)-2-oxo-4-n-propyl-1-pyrrolidinyl)butanamide (Overall yield: 80%).

EXAMPLE 2

Synthesis of (2S)-2-((4R)-2-oxo-4-n-propyl-1-pyrrolidinyl)butanamide

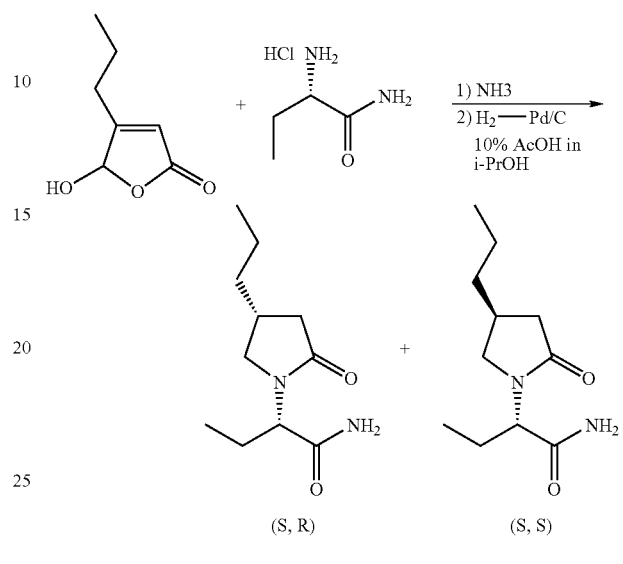

Example 1 is repeated except that in step 1.1 a solution of (2S)-2-aminobutyramide.HCl in isopropanol is used (27.72 g, 1.2 equivalent), which is neutralised with a $NH_3$/isopropanol solution (3.4-3.7 mol/L). The resulting ammonium chloride is removed from this solution by filtration and the solution is directly used for reaction with 5-hydroxy-4-n-propyl-furan-2-one (23.62 g, 1.0 equivalent) without intermediate drying of the (2S)-2-aminobutyramide solution. Yield after separation of the two diastereoisomers and recrystallisation: approximately 84%.

EXAMPLE 3

Synthesis of (S)-(-)-α-ethyl-2-oxo-1-pyrrolidine acetamide

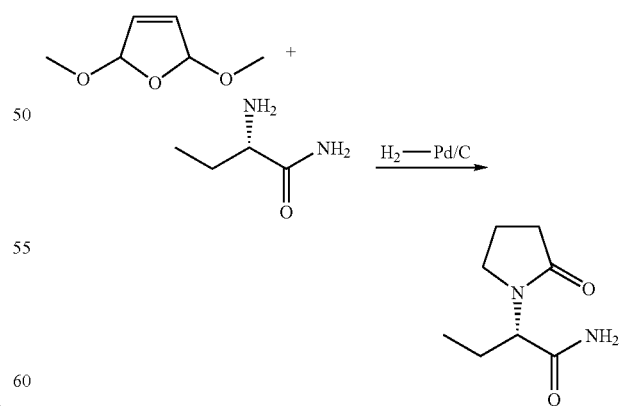

(2S)-2-Aminobutyramide free base (2 g) is dissolved in water (80 ml) and 2,5-dimethoxy-2,5-dihydro furan is added (2.4 ml, 1 eq.). Aqueous HCl (2.4 ml, 1.5 eq.) is added at room temperature and the reaction mixture is stirred for 1.5 hours. Sodium carbonate is then added until the pH of the mixture reaches 8-9. Then, a Pd/C (5%) catalyst in a mixture of water and ethanol (20 ml) is added together with H$_2$ and maintained during 35 minutes. The solution is cooled between 15° C. and 25° C. and filtered to remove the catalyst.

Ethanol is removed under vacuum and the desired compound extracted with ethyl acetate; the organic solution is then washed with brine, dried over magnesium sulfate and evaporated to give (S)-(−)-α-ethyl-2-oxo-1-pyrrolidine acetamide (Yield: 13%).

EXAMPLE 4

Synthesis of methyl 1-[(1S)-1-(aminocarbonyl)propyl]-5-oxo-3-pyrrolidinecarboxylate

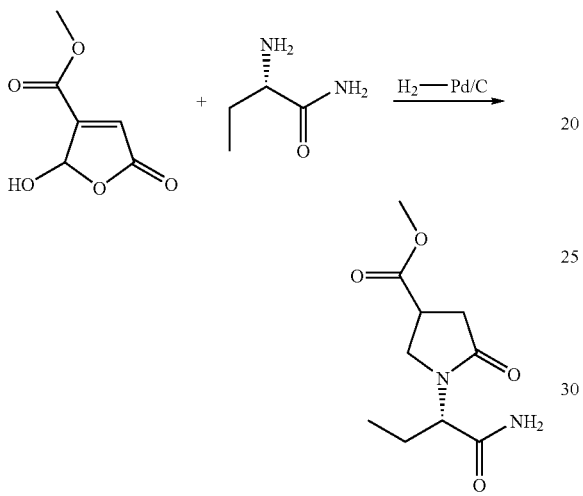

2-Hydroxy-5-oxo-2,5-dihydro-furan-3-carboxylic acid methyl ester (3.08 g) in methanol (40 ml) is added to a solution of (2S)-2-aminobutyramide (2.0 g) in methanol (30 ml) in a hydrogenation reactor and the mixture is maintained for at least 2 hours at room temperature. Then Pd/C catalyst (10 w/w %; Johnson Matthey 5% Pd on carbon—type 87L) is added and hydrogen introduced into the system under pressure. The temperature is kept at 40° C. maximum and the hydrogen pressure between 4 bar and 5 bar, followed by stirring for at least 20 hours following the initial reaction. The solution is then cooled between 15° C. and 25° C. and filtered to remove the catalyst. The solvent is evaporated under vacuum and the resulting yellow product is purified by preparative liquid chromatography (eluent: dichloromethane/methanol (95:5)) (Yield 43%).

The invention claimed is:

1. A process for the preparation of 2-oxo-1-pyrrolidine derivatives of general formula (I), and salts thereof, wherein:

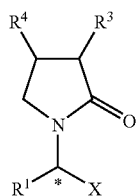

R$^1$ is R$^a$ or R$^b$;
R$^3$ and R$^4$ are the same or different and each is, independently, hydrogen, hydroxy, thiol, halogen, cyano, carboxy, sulfonic acid, R$^a$, R$^b$, alkylsulfonyl, arylsulfonyl, alkylsulfinyl, arylsulfinyl, alkylthio, arylthio, alkoxy, aryloxy, sulfonamide, acyl, ester, amido, acyloxy, esteroxy or amidooxy;

X is —CONR$^5$R$^6$, —COOR$^7$ or —CN;
R$^5$, R$^6$, R$^7$ are the same or different, and each is, independently, hydrogen, R$^a$ or R$^b$;
R$^a$ is C1-20 alkyl or C1-20 alkyl substituted by one or more hydroxy, thiol, halogen, cyano, carboxy, sulfonic acid, R$^b$, alkylsulfonyl, arylsulfonyl, alkylsulfinyl, arylsulfinyl, alkylthio, arylthio, alkoxy, aryloxy, sulfonamide, acyl, ester, amido, acyloxy, esteroxy and/or amidooxy;
R$^b$ is aryl, heteroaryl, heterocycloalkyl or the same substituted by one or more R$^a$, hydroxy, thiol, halogen, cyano, carboxy, sulfonic acid, aryl, alkylsulfonyl, arylsulfonyl, alkylsulfinyl, arylsulfinyl, alkylthio, arylthio, alkoxy, aryloxy, sulfonamide, heterocycloalkyl, heteroaryl, acyl, ester, amido, acyloxy, esteroxy and/or amidooxy;

comprising the reaction of a furan derivative of formula (II) or (III)

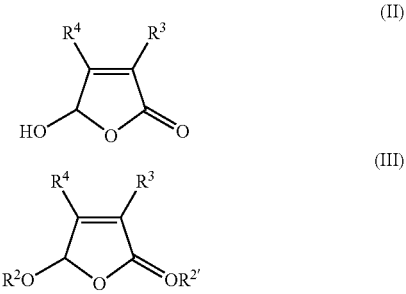

wherein R$^2$ and R$^{2'}$ are the same or different and each is C1-10 alkyl or the same substituted by aryl, with a compound of formula (IV)

and with H$_2$ in the presence of catalyst.

2. The process according to claim 1, wherein a furan derivative of formula (II) is used.

3. The process according to claim 1, wherein R$^3$ is hydrogen.

4. The process according to claim 2, wherein R$^4$ is R$^a$ or hydrogen.

5. The process according to claim 4, wherein R$^4$ is C1-6 alkyl or C1-6 alkyl substituted by one or more halogens.

6. The process according to claim 5, wherein R$^4$ is n-propyl.

7. The process according to claim 1, wherein X is —CONR$^5$R$^6$.

8. The process according to claim 7, wherein X is —CONH$_2$.

9. The process according to claim 1, wherein R$^1$ is C1-6 alkyl.

10. The process according to claim 9, wherein R$^1$ is ethyl.

11. The process according to claim 2, wherein the compound of formula (II) is obtained by reaction of an aldehyde of formula (V) with a ketoacid of formula (VI),

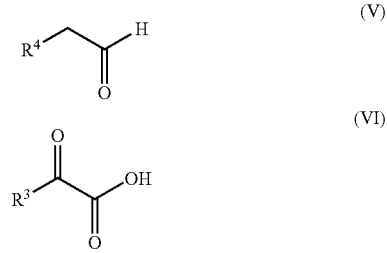

wherein $R^3$ and $R^4$ are as defined in claim 1, in the presence of a base.

12. The process according to claim 1, wherein the compound of formula (IV) is obtained by neutralisation of the corresponding hydrochloride salt.

13. The process according to claim 1, wherein the catalyst is a Pd, Pt or Ni based catalyst.

14. The process according to claim 13, wherein the catalyst is a Pd based catalyst.

15. The process according to claim 1, wherein compounds of formula (I) are in the (S)-form or in the (R)-form.

16. The process according to claim 15, wherein compounds of formula (I) are in the (S)-form.

17. The process according to claim 1, wherein when $R^3$ and/or $R^4$ are different from hydrogen the obtained diastereoisomers are further separated.

18. The process according to claim 1, which is applied to the preparation of (2S)-2-((4R)-2-oxo-4-n-propyl-1-pyrrolidinyl)butanamide.

* * * * *

UNITED STATES PATENT AND TRADEMARK OFFICE
CERTIFICATE OF CORRECTION

| | | |
|---|---|---|
| PATENT NO. | : 7,629,474 B2 | Page 1 of 1 |
| APPLICATION NO. | : 10/572579 | |
| DATED | : December 8, 2009 | |
| INVENTOR(S) | : John Surtees et al. | |

It is certified that error appears in the above-identified patent and that said Letters Patent is hereby corrected as shown below:

In column 2, lines 15-20, formula (III):

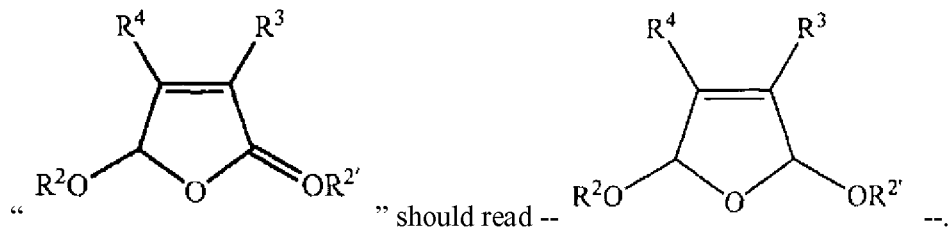

In column 10, lines 31-36, formula (III):

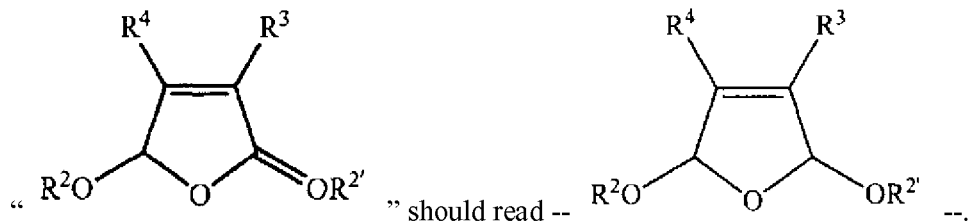

Signed and Sealed this
Tenth Day of April, 2012

David J. Kappos
*Director of the United States Patent and Trademark Office*